US00PP09071P

United States Patent [19]

Winchel

[11] Patent Number: Plant 9,071

[45] Date of Patent: Mar. 14, 1995

[54] HYBRID TEA ROSE PLANT NAMED WEKFRAG

[75] Inventor: Joseph Winchel, Harbor City, Calif.

[73] Assignee: Weeks Wholesale Rose Grower, Inc., Upland, Calif.

[21] Appl. No.: 157,962

[22] Filed: Nov. 24, 1993

[51] Int. Cl.[6] ..... A01H 5/00

[52] U.S. Cl. ..... Plt./20

[58] Field of Search ..... Plt. 20, 19, 11

*Primary Examiner*—Howard J. Locker

*Attorney, Agent, or Firm*—Christie, Parker & Hale

[57] ABSTRACT

A new variety of Hybrid Tea rose suitable for garden decoration, having flowers of light red/deep pink coloration.

1 Drawing Sheet

BACKGROUND OF THE INVENTION

This invention relates to a new and distinct variety of Hybrid Tea Rose. The varietal denomination of the new variety is 1 Wekfrag.' The plant is bushy and upright growing and may be cultivated for outdoor garden decoration. It was bred in Harbor City, Calif., and has an unknown seed parent and as its pollen parent the variety known as 'Dolly Parton' (U.S. Plant Pat. No. 5,608).

SUMMARY OF THE INVENTION

The new variety cv. 'Wekfrag' may be distinguished from other presently available and known commercial rose cultivars by the following combination of characteristics: abundant production of heavily fragrant blended light red/deep pink flowers and moderately narrow leaflets held on a long rachis. Cv. 'Wekfrag' may be propagated by cuttings, budding, grafting and tissue culture.

Asexual propagation of the new variety as performed by budding in Kern County and Upland, Calif., shows that the foregoing and other distinguishing characteristics come true to form and are established and transmitted through succeeding propagations.

Comparison with Parent Varieties

The seed parent is unknown.

The new variety may be distinguished from its pollen parent, 'Dolly Parton', by the following combination of characteristics: whereas the new seedling bears flowers of a light red/deep pink coloration, the pollen parent bears flowers of a dark orange coloration; 'Dolly Parton' has a plant with only moderate vigor and branching, whereas 'Wekfrag' has a plant with significantly stronger vigor that produces more flowers and fuller branching.

BRIEF DESCRIPTION OF THE ILLUSTRATION

The accompanying photograph illustrates the plant in color and shows the flowering thereof from bud to full bloom depicted in color as nearly correct as it is possible to make in a color illustration of the character. Throughout this specification, names are values based upon the Colour Chart of The Royal Horticultural Society of London, England, except where common terms of color definition are employed.

DESCRIPTION OF THE NEW VARIETY

The following descriptive matter pertains to roses of the new cultivar grown outdoors on September 1993, in Upland, Calif. Phenotype expression may vary with environmental, cultivar and climatic conditions as well as differences in conditions of light and soil.

FLOWER

The new variety bears its flowers usually singly, sometimes two to three or more per stem. Flowers are borne in irregular rounded clusters on normal strength medium to long stems for the class. Outdoors the plant blooms abundantly and nearly continuously during the growing season. The flowers have a strong fruity to spicy fragrance.

BUD

The peduncle is of average to long length for the class, of average caliper, and usually erect and stiff but sometimes bending as the flower matures. It is moderately smooth with few stipitate glands and very few small prickles. Peduncle color is between 144A and 138B sometimes lightly washed with near 183C.

Before the calyx breaks, the bud is of medium to large size for the class, medium to long in length, and pointed to ovoid in shape. The surface of the bud bears some foliaceous appendages and many stipitate glands usually with slender foliaceous parts extending beyond the tip of the bud equal to ½ or more of its length. Bud color is between 144A and 138B.

The inner surface of the sepals is covered with fine wooly tomentum; sepal margins are lined with some stipitate glands.

As the first petal opens, the bud is moderately large for the class, medium to long in length, and very pointed to ovoid in form. The color of the outside and inside surfaces of the newly opened petals is between 46B and 47 A with a medium sized basal attachment zone of near 5B. It does open up well but can be moderately retarded from opening by wet cold weather.

BLOOM

When fully open, the bloom is moderately large for the class, ranging from 10 to 12 cms. in diameter. Petalage is moderately double with 36 to 41 petals and 1 to 4 petaloids arranged regularly. When partially open, the bloom form is full to high centered and the patals are moderately spiraled with petal edges somewhat reflexed outward. When fully open, the bloom form is moderately full to globular, and the petals are somewhat cupped to undulated with petal edges moderately reflexed outward.

PETALS

The petals are of somewhat heavy substance and of medium thickness, with inside surfaces slightly velvety and outside surfaces slightly shiny to satiny. The outer petals are nearly round in shape with rounded apices. The inside petals are somewhat round to broadly obovate in shape with apices mostly rounded sometimes slightly notched with one to two notches.

NEWLY OPENED FLOWER

The outside surface of the outer, intermediate and inner petals is between 53C and 51A. The outside and inside surface of the outer, intermediate and inner petals has a medium sized basal attachment zone of near 5C.

The inside surface of the outer petals is between 47D and 51B with a moderately large area toward the petal edge blushed with between 53B and 51A. The inside surface of the intermediate petals is between 47D and 51B with a smaller area toward the petal edge blushed with between 53B and 51A. The inside surface of the inner petals is between 47D and 51B with no blushing.

The general tonality of the newly opened flower is between 47D and 51B with the outermost petals blushed to between 53B and 51A.

THREE DAY OLD FLOWER

The outside surface of the outer and inner petals is between 58C and 54B. The outside and inside surface of the outer and inner petals has a medium sized basal attachment zone of near 2D.

The inside surface of the outer petals is between 54B and 55A with some blushing toward the edge of the petal with between 53C and 54A. The inside surface of the inner petals is between 54B and 55A with a smaller area at the petal edge of a similarly colored blush.

The general tonality of the three day old flower is between 54B and 55 A with some blushing on the outermost petals of between 53C and 54A.

On the spent bloom, the petals usually drop off cleanly.

In September, blooms on the bush growing in the garden generally last from three to four days. Cut roses grown outdoors and kept at normal indoor living temperatures generally last from three to four or more days.

MALE REPRODUCTIVE ORGANS

Stamens are many in number and are arranged regularly about the pistil. The filaments are of moderately uneven length ranging from medium to long, most with anthers. The anthers are medium for the class and all open approximately at the same times. Another color is near 4B when immature and near 162C at maturity. Pollen is somewhat sparse and near 4D in color.

FEMALE REPRODUCTIVE ORGANS

Pistils are average to many in number (approximately 110). The styles are somewhat uneven, average to long in length, somewhat thin to average in caliper, and very loosely bunched. Stigma color is near 2D. Style color is near 48D. Ovaries are usually most enclosed in the calyx, although some may protrude from the calyx. Hips have not been observed on this variety when grown in Upland, Calif.

FOLIAGE

The compound leaves are usually comprised of three to five and sometimes seven leaflets and are borne in normal quantities. The leaves are medium sized for the class, moderately heavy in texture, and matte in finish. The leaflets are shaped somewhat narrowly oval to ovate with moderately acute apices and somewhat rounded bases. Their margins are irregular to doubly serrate. By "irregular" is meant that the leaf margin varies from dentate to serrate on the same leaf.

The upper surface of the mature leaf is between 139A and 147A. The under surface of the mature leaf is between 138B and 191C. The upper surface of the young leaf is between 146A and 137A, somewhat heavily suffused with near 183B. The under surface of the young leaf is of similar coloration but very heavily suffused with near 183B.

The rachis is moderately long, somwehat light to average in caliper and moderately smooth with some stipitate glands on the edges of the upper side. The under side of the rachis is moderately rough with many stipitate glands and 3 to 4 small prickles.

The stipules are very long in length with moderately narrow somewhat short points that usually turn out at an angle of less than 90 degrees.

The plant displays an average degree of resistance to blackspot and rust as compared to other commercial varieties grown under comparable conditions in Upland, Calif.

GROWTH

The plant has a bushy upright medium height habit with moderately full branching. It displays very vigorous growth and the canes are of medium caliper for the class.

The color of the major stems are between 146B and 152B. They bear few to several large prickles which are of medium length for the class. The large prickles are almost straight angled moderately downward with a very long narrow base; prickle color is between 166A and 177A.

The color of the branches are between 146B and 144A. They bear several large prickles which are of medium length for the class. The large prickles are almost straight angled moderately downward with a very long narrow base; prickle color is near 165C. The branches bear few small prickles of similar shape and coloration.

The color of the new shoots are between 146C and 144B often heavily suffused with near 183C. They bear several large prickles which are of medium length for the class. The large prickles are almost straight angled moderately downward with a very long narrow base; prickle color is near 184C. The shoots also bear few small prickles of similar shape and coloration.

As indicated previously, the stems are medium to long, 30 to 40 cm; the peduncle is average to long, 7 to 11 cm. The green bud is considered medium to large, with a diameter at the widest point of 3 to 4 cm and medium to long in length, 4 to 5 cm. A just-opening bud is moderately large, 3.5 to 4.5 cm at the widest point and medium to long in length, about 5 cm. The bloom is moderately large, 10 to 12 cm in diameter. Leaflets of the leaves are 3 to 7 cm long (the terminal leaflet being the longest) and 1.5 to 4.5 cm in width at the widest point. The leaves are medium-sized (10 to 14 cm long and 8 to 12 cm wide at the widest point). The plant has a medium growth habit reaching 95 to 120 cm in height and 75 to 95 cm in width.

I claim:

1. A new and distinct variety of Hybrid Tea rose plant substantially as described and illustrated herein.

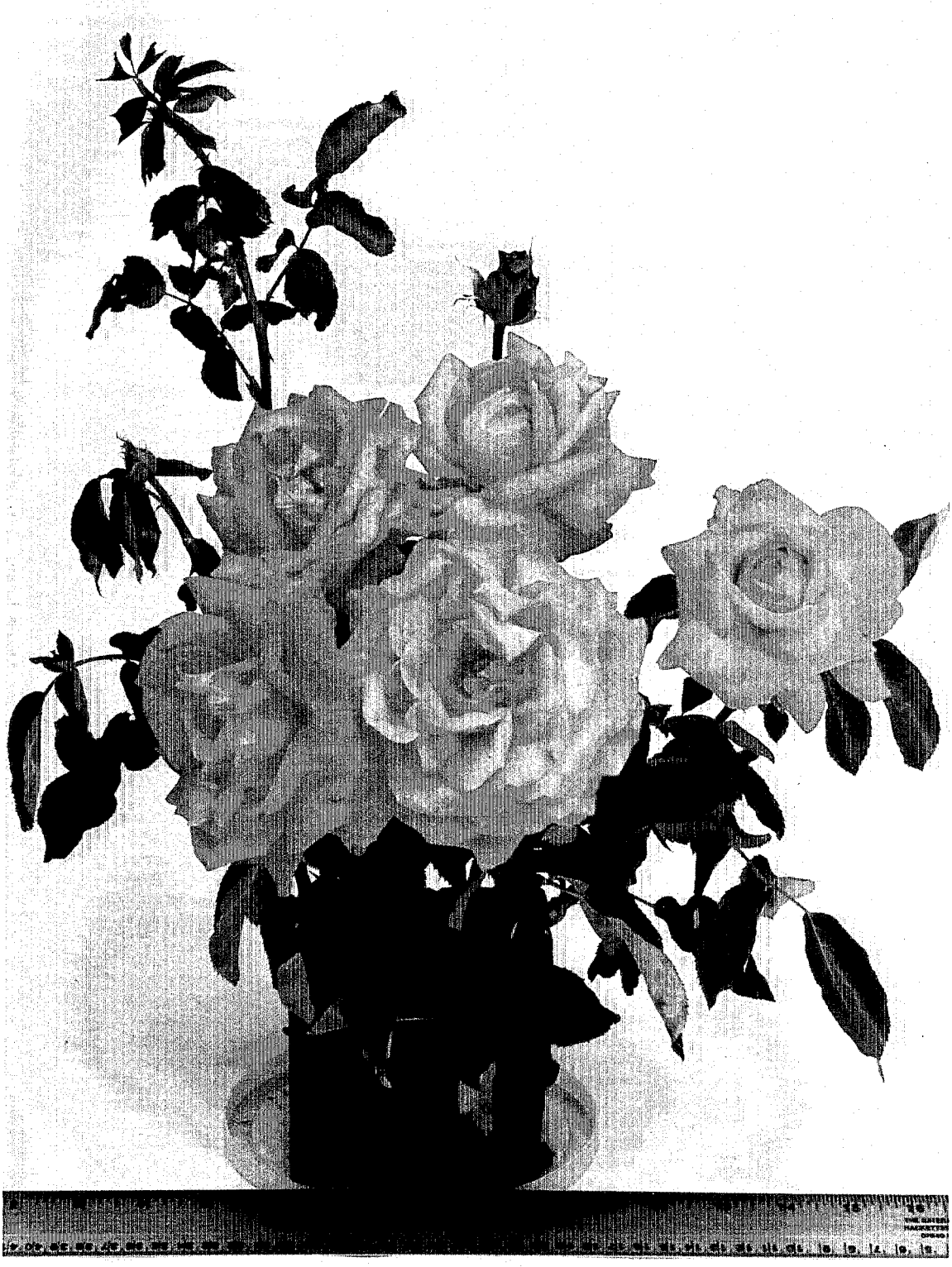

* * * * *